(12) United States Patent
Horn

(10) Patent No.: US 8,043,209 B2
(45) Date of Patent: Oct. 25, 2011

(54) SYSTEM AND METHOD FOR TRANSMITTING THE CONTENT OF MEMORY STORAGE IN AN IN-VIVO SENSING DEVICE

(75) Inventor: Eli Horn, Kiryat Motzkin (IL)

(73) Assignee: Given Imaging Ltd., Yoqneam (IL)

( * ) Notice: Subject to any disclaimer, the term of this patent is extended or adjusted under 35 U.S.C. 154(b) by 1165 days.

(21) Appl. No.: 11/451,397

(22) Filed: Jun. 13, 2006

(65) Prior Publication Data

US 2007/0287891 A1 Dec. 13, 2007

(51) Int. Cl.
*A61B 1/04* (2006.01)

(52) U.S. Cl. ......................................... 600/109

(58) Field of Classification Search .................. 600/109, 600/118, 160, 302, 117
See application file for complete search history.

(56) References Cited

U.S. PATENT DOCUMENTS

| | | | |
|---|---|---|---|
| 3,683,389 A | 8/1972 | Hollis | |
| 3,971,362 A | 7/1976 | Pope et al. | |
| 4,278,077 A | 7/1981 | Mizumoto | |
| 4,689,621 A | 8/1987 | Kleinberg | |
| 4,741,327 A | 5/1988 | Yabe | |
| 4,844,076 A | 7/1989 | Lesho et al. | |
| 5,279,607 A | 1/1994 | Schentag et al. | |
| 5,311,305 A * | 5/1994 | Mahadevan et al. | 348/169 |
| 5,604,531 A | 2/1997 | Iddan et al. | |
| 5,819,736 A | 10/1998 | Avny et al. | |
| 6,240,312 B1 | 5/2001 | Alfano et al. | |
| 6,276,798 B1 * | 8/2001 | Gil et al. | 351/206 |
| 6,320,583 B1 * | 11/2001 | Shaw et al. | 345/619 |
| 7,009,634 B2 | 3/2006 | Iddan et al. | |
| 7,116,352 B2 * | 10/2006 | Yaron | 348/45 |
| 7,187,049 B2 * | 3/2007 | Sarwari | 257/431 |
| 7,195,588 B2 * | 3/2007 | Homan et al. | 600/118 |
| 7,629,659 B2 * | 12/2009 | Jacobsen et al. | 257/432 |
| 7,664,174 B2 * | 2/2010 | Avni et al. | 375/240.01 |
| 2001/0017649 A1 | 8/2001 | Yaron | |
| 2001/0051766 A1 | 12/2001 | Gazdzinski | |
| 2002/0093484 A1 | 7/2002 | Skala et al. | |
| 2002/0158976 A1 | 10/2002 | Avni et al. | |
| 2002/0171669 A1 | 11/2002 | Meron et al. | |
| 2002/0198439 A1 | 12/2002 | Mizuno | |
| 2003/0018280 A1 | 1/2003 | Lewkowicz et al. | |
| 2003/0028078 A1 | 2/2003 | Glukhovsky | |

(Continued)

FOREIGN PATENT DOCUMENTS

DE 34 40 177 5/1986

(Continued)

OTHER PUBLICATIONS

Robots for the future—Shin-Ichi, et al., Nov. 29, 2001.

(Continued)

*Primary Examiner* — Philip Smith
(74) *Attorney, Agent, or Firm* — Pearl Cohen Zedek Latzer, LLP

(57) ABSTRACT

A method and system for in-vivo sensing includes transmitting data that relates to data stored in a memory area located in the sensing device. The data that relates to data stored in a memory area may be transmitted in a data block, and the data block may include sensory data. The data that relates to data stored in a memory area may be received, recorded, displayed, processed or used in any suitable way, for example, to generate commands to the sensing device.

6 Claims, 5 Drawing Sheets

U.S. PATENT DOCUMENTS

| | | | |
|---|---|---|---|
| 2003/0117491 A1* | 6/2003 | Avni et al. | 348/77 |
| 2003/0151661 A1 | 8/2003 | Davidson et al. | |
| 2004/0242962 A1* | 12/2004 | Uchiyama | 600/118 |
| 2005/0049461 A1 | 3/2005 | Honda et al. | |
| 2005/0075537 A1* | 4/2005 | Chen et al. | 600/109 |
| 2005/0110881 A1* | 5/2005 | Glukhovsky et al. | 348/231.99 |
| 2005/0159643 A1* | 7/2005 | Zinaty et al. | 600/109 |
| 2005/0259487 A1* | 11/2005 | Glukhovsky et al. | 365/202 |
| 2005/0288595 A1 | 12/2005 | Bettesh | |
| 2006/0017826 A1* | 1/2006 | Sekimoto et al. | 348/246 |
| 2006/0189843 A1* | 8/2006 | Nakamura et al. | 600/118 |
| 2008/0074491 A1* | 3/2008 | Matsui | 348/65 |
| 2008/0100698 A1* | 5/2008 | Mori et al. | 348/65 |
| 2008/0200757 A1* | 8/2008 | Glukhovsky et al. | 600/109 |
| 2008/0292150 A1* | 11/2008 | Hirakawa | 382/128 |
| 2009/0073273 A1* | 3/2009 | Wang et al. | 348/222.1 |
| 2009/0074310 A1* | 3/2009 | Miaou et al. | 382/236 |
| 2009/0097725 A1* | 4/2009 | Krupnik et al. | 382/128 |
| 2009/0167908 A1* | 7/2009 | Mori et al. | 348/251 |
| 2009/0225158 A1* | 9/2009 | Kimoto | 348/77 |
| 2009/0322865 A1* | 12/2009 | Wang et al. | 348/68 |

FOREIGN PATENT DOCUMENTS

| | | |
|---|---|---|
| JP | 57-45833 | 3/1982 |
| JP | HEI 3-289779 | 12/1991 |
| JP | HEI 4-109927 | 4/1992 |
| JP | HEI 4-180736 | 6/1992 |
| JP | 7289504 | 11/1995 |
| JP | 2001 137182 | 5/2001 |
| JP | 2001 224551 | 8/2001 |
| JP | 2001224553 | 8/2001 |
| WO | WO 92/21307 | 12/1992 |
| WO | WO 98/11816 | 3/1998 |
| WO | WO 00/22975 | 4/2000 |
| WO | WO 01/08548 | 2/2001 |
| WO | WO 01/50941 | 7/2001 |
| WO | WO 01/65995 | 9/2001 |
| WO | WO 02/067593 | 8/2002 |
| WO | WO 02/094337 | 11/2002 |
| WO | WO 03/003706 | 1/2003 |

OTHER PUBLICATIONS

The Radio Pill, Rowlands, et al., British Communications and Electronics, Aug. 1960, pp. 598-601.

Video Camera to "TAKE"—RF System lab. Dec. 25, 2001.

Wellesley company sends body montiors into space—Crum, Apr. 1998.

www.rfnorkia.com—NORIKA3, Dec. 24, 2001.

Wireless transmission of a color television moving image from the stomach using a miniature CCD camera, light source and microwave transmitter. Swain CP, Gong F, Mills TN. Gastrointest Endosc 1997;45:AB40.

BBC News Online—Pill camera to 'broadcast from the gut', Feb. 21, 2000, www.news.bbc.co.uk.

Wang, et al., "Integrated Micro-Instrumentation for Dynamic Monitoring of the Gastro-Intestinal Tract", Presented at IEEE Instrumentation and Measurement Technology Conference, May 2002, Anchorage, AK, USA, www.see.ed.ac.uk/Naa.publications.html.

Hang Iiu et al, "Error control schemes for networks: an overview", Mobile Networks and Applications 2 (1997), p. 167-182.

* cited by examiner

SYSTEM AND METHOD FOR TRANSMITTING THE CONTENT OF MEMORY STORAGE IN AN IN-VIVO SENSING DEVICE

FIELD OF THE INVENTION

The present invention relates to an apparatus and method for in-vivo imaging.

BACKGROUND OF THE INVENTION

In-vivo devices, such as, for example, capsules, may be capable of gathering information regarding a body lumen while inside the body lumen. Such information may be, for example, a stream of data or image frames from the body lumen and/or measurements of parameters that are medically useful, such as, for example, pH. A sensing device may transmit the gathered information via a hard-wired or wireless medium, and the gathered information may be received by a receiver/recorder. The recorded information may be sent from the receiver/recorder to a workstation to be analyzed and/or displayed.

Such a system may be operated by, for example, health care professionals and technicians, in a hospital, or another health facility.

SUMMARY OF THE INVENTION

An exemplary embodiment of the present invention provides a system and method for transmitting data that relates to data stored in a memory area located in the sensing device such as the status of the sensing device. This data may be transmitted in a data block, wherein the data block may include sensory data. This data may be received, recorded, displayed, processed or used in any suitable way, for example, to generate commands to the sensing device.

BRIEF DESCRIPTION OF THE DRAWINGS

Embodiments of the invention are illustrated by way of example and not limitation in the figures of the accompanying drawings, in which like reference numerals indicate corresponding, analogous or similar elements, and in which.

Figure 1:
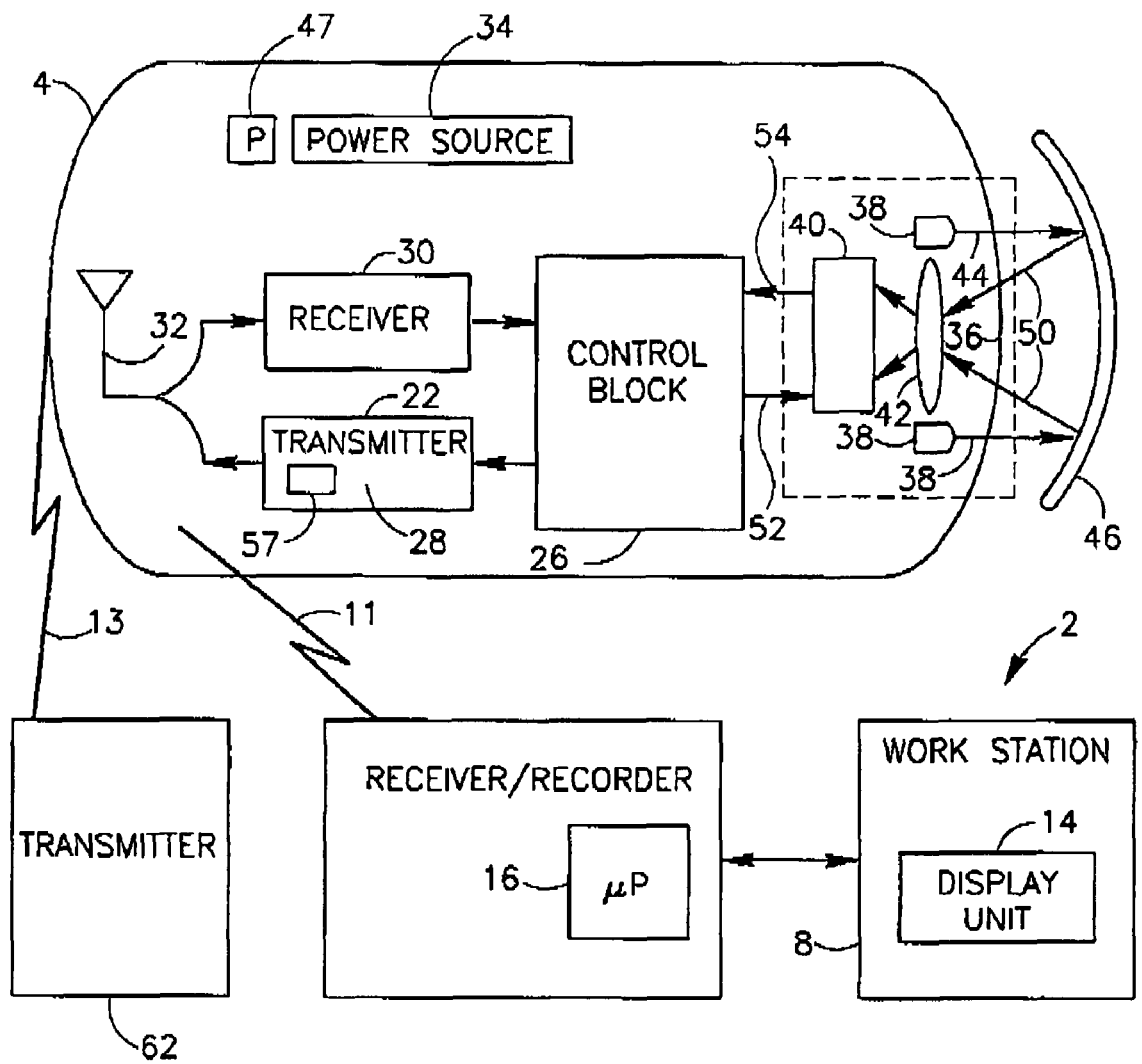
FIG. 1 is a simplified illustration of an exemplary in-vivo sensing system, including an in-vivo sensing device, a receiver/recorder and a workstation, in accordance with some embodiments of the invention.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION OF THE INVENTION

In the following detailed description, numerous specific details are set forth in order to provide a thorough understanding of embodiments of the invention. However it will be understood by those of ordinary skill in the art that the embodiments of the invention may be. practiced without these specific details. In other instances, well-known methods, procedures, components and circuits have not been described in detail so as not to obscure the embodiments of the invention.

Unless specifically stated otherwise, as apparent from the following discussions, it is appreciated that throughout the specification discussions utilizing terms such as "processing," "computing," "calculating," "determining," or the like, refer to the action and/or processes of a workstation, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

A system according to some embodiments of the invention may include an in-vivo sensing device, such as an imaging device, or a device for sensing physiological parameters of a body lumen such as, pH, temperature, pressure, electrical impedance, etc. The sensing device may generate sensory data, for example, image data that relates to an image, a frame or a stream of images or frames. A transmitter, for example, in the sensing device, may transmit sensory data generated by the sensing device. A receiver, which may be positioned close to or worn on a subject, that may receive streams of data transmitted by the transmitter in the sensing device. A workstation that may accept, process and/or display the data from the receiver, which may include sensed data (e.g., image data) and/or data stored in memory areas. A workstation may download or access the stream of data from the receiver/recorder and may analyze and/or display the stream of data. In one embodiment, the workstation may download, store, use or display the stream of image data separately from the stream of memory data.

According to embodiments of the present invention an in-vivo sensing device may include one or more memory areas. A memory area may be or include, for example, a storage area in an element of a device or system, for example, one or more registers, cache units or other types of memories. Memory areas may be located in an imager, a transmitter, a control block or separate storage area in an in-vivo sensing device. Memory areas may store memory data, which may include any data of interest, for example, sensory or non-sensory data. Non-sensory data may relate to the states or status of the sensing device or the sensory data that the sensing device generates, but is not sensory data. For example, a set of image data may be used to produce an image frame, whereas non-image data typically may not be used to produce the image frame directly, but may affect image display. Instead, the non-image data, for example, transmitted with or in the same data block or imaging period as image data, may provide information relating to the image data or the state of the imaging device when it generates the image data. Memory areas may store one or more units of memory data, typically of a fixed size. Memory areas may access or may include pointers to data stored in external memory locations and may contain addresses of appropriate external memory locations. Memory data may include read only data (e.g., including the status of the sensing device) or read/write data.

Memory areas may store permanent data which is typically not updated. Permanent data may indicate static properties of the sensing device. Permanent data may include, for example, the mode, resolution, or formatting of the sensory data generated by the sensing device. Permanent data typically includes read only data Memory areas may store temporary data, which may be updated, for example, periodically or in response to a request or command. Temporary data may indicate dynamic properties of the sensing device, for example, shutter speed, sensor temperature, light pulse width, analogue gain, average intensities of the sensory data generated by the sensing device, or variable settings. Temporary data may be generated, for example, by a processor in the sensing device. Temporary data may include, read only data, write only data or read/write data.

In one embodiment, memory areas may store scrambling data provided by for example a scrambling circuit as is known in the art, which may be used to protect data stored in memory areas. Data stored in memory areas and/or transmitted may be scrambled or scrambling data. In one embodiment, memory areas may store error detection or correction data such as error correction code (ECC) or cyclic redundancy check (CRC) data as is know in the art.

A transmitter, for example, in an in-vivo sensing device, may transmit memory data or values that, for example, may be added to or attached to sensory data, for example, streams of image data corresponding to image frames. Memory data may be said to correspond to image data if the memory data and image data are generated substantially at the same time or if the memory data relates to the state of operations, data or devices substantially at the time that the sensing device generated the image data. The memory data may be attached to or transmitted with substantially every image data transmission from sensing device. For example, a transmitted data block may include memory data, which may be attached or added at the end of a stream of image data, for example, that corresponds to an image frame. In one embodiment, the transmitted memory data may be a line of data that may include the current state of some or all memory areas located in the sensing device. A receiver may accept the transmitted data and send it to a workstation where it may be stored, processed, displayed or used in any other suitable manner.

A transmitter, for example, in the sensing device, may transmit sensory data generated by the sensing device and non-sensory data stored in the imaging device, for example, in one or more memory or register areas. In one embodiment, the transmitter may transmit sensory data and non-sensory data in the same imaging period or one or more data blocks or image streams.

Devices according to embodiments of the present invention may be similar to embodiments described in U.S. Pat. No. 7,009,634 to Iddan et al., entitled "Device for In-Vivo Imaging", and/or in U.S. Pat. No. 5,604,531 to Iddan et al., entitled "In-Vivo Video Camera System", and/or in U.S. patent application Ser. No. 10/046,541, filed on Jan. 16, 2002, published on Aug. 15, 2002 as U.S. Patent Application Publication No. 2002/0109774, all of which are hereby incorporated by reference. An external receiver/recorder unit, a processor and a workstation, such as those described in the above publications, may be suitable for use with some embodiments of the present invention. Devices and systems as described herein may have other configurations and/or other sets of components. For example, some embodiments of the present invention may be practiced using an endoscope, needle, stent, catheter, etc. In vivo devices, according to some embodiments, may be capsule shaped, or may have other shapes, for example, a peanut shape or tubular, spherical, conical, or other suitable shapes.

Reference is made to FIG. 1, which is a simplified illustration of an exemplary in-vivo sensing system 2, including an in-vivo sensing device 4, a receiver/recorder 6, and a workstation 8, in accordance with an embodiment of the invention. Receiver/recorder 6 may include a processor (uP) 16 to, for example, control, at least in part, the operation of receiver/recorder 6. According to some embodiment of the invention, sensing device 4 may be a capsule, although, other configurations are possible.

Sensing device 4 may include a control block 26, a transmitter 28, a receiver 30, a processor 47, an antenna 32, a power source 34, and an imaging system 24 that may include, for example, an optical window 36, at least one illumination source 38, such as, for example, a light emitting diode (LED), an imager 40, and an optical system 42. Sensing device 4 may include one or more memory areas 57, for example memory units, registers, etc. Memory areas 57 may be located in imager 40, transmitter 28, control block 26 and/or other or separate storage areas in sensing device 4. In one embodiment, all of the components of sensing device 4 are sealed within a device body (the body or shell may include more than one piece); for example, an imager 40, illumination source 38, power source 34, control block 26, a receiver 30, a transmitter 28, an antenna 32, an optional processor 47, and any other suitable components may all be sealed within the device body.

Sensing device 4 may gather information, such as, for example, image data or a stream of images, while inside a patient's body. Sensing device 4 may also store data in memory areas 57. Data stored in memory areas 57 may include, for example, data that relates to the state of sensing device 4 or components of sensing device 4 at the time the image data was gathered or may access or include pointers to data stored in external or other memory locations. Memory areas may store data that has a fixed size. Such data may be transmitted to receiver/recorder 6 via a wireless or hard-wired medium 11 while inside the patient's body, for example, by transmitter 28.

Data stored in memory areas 57 may be transmitted, for example, along with sensory data, by transmitter 28. Receiver/recorder 6 may record information received from sensing device 4.

Sensing device 4 may transmit sensory data, for example, image data, and corresponding memory data in substantially the same data block or image stream. In another embodiment, sensing device 4 may transmit image data and corresponding memory data within an imaging period. An imaging period may be for example a period of time during which an imaging device captures and generates and/or transmit image data that relates to an image, a frame, a stream of images, one or more data blocks or any other suitable grouping of image data. Within an imaging period an in-vivo imaging device may capture image or other sensory data and transmit image data generated by the imaging device and a subset of non-image data stored in the imaging device, for example, data stored in one or more memory areas 57. Sensing device 4 may operate across a series of imaging periods, for example, capturing and transmitting two frames a second. Other imaging rates may be used.

Workstation 8 may receive recorded information from receiver/recorder 6 via, for example, a wireless or hard-wired medium 12, and may process and/or present information received from receiver/recorder 6 to an operator. For example, workstation 8 may include one or more display units 14, and may display the memory data and/or the stream of images recorded in receiver/recorder 6 on display units 14. In one embodiment, the memory data or a derivation thereof and the corresponding stream of images may be displayed substantially simultaneously and, for example, substantially adjacently. Thus, the viewer may monitor the relationship between the state of sensing device 4 and the corresponding images.

In one embodiment, receiver/recorder 6, workstation 8 or the viewer by entering data into workstation 8, may use this information to generate, control or transmit signals or commands to sensing device 4, for example, via a transmitter 62, which may be located inside or outside of receiver/recorder 6. Transmitter 62 may transmit from a location external to sensing device 4 to a receiver 30 inside sensing device 4, inside the patient's body, via a wireless or hard-wired medium 13. Sensing device 4 may store, process or use the data, instructions or commands received by receiver 30 in any suitable manner in accordance with embodiments of the present invention.

Sensing device 4 typically may be or may include an autonomous swallowable capsule, but sensing device 4 may have other shapes and need not be swallowable or autonomous. Embodiments of sensing device 4 are typically autonomous, and are typically self-contained. For example, sensing device 4 may be a capsule or other unit where all the components including for example power components are substantially contained within a container or shell, and where sensing device 4 does not require any wires or cables to, for example, receive power or transmit information. Sensing device 4 may communicate with an external receiving and display system to provide display of data, control, or other functions. For example, in an autonomous system power may be provided by an internal battery or a wireless receiving system. Other embodiments may have other configurations and capabilities. For example, components may be distributed over multiple sites or units. Control information may be received from an external source.

A non-exhaustive list of examples of memory areas 57 includes, for example, semiconductor devices such as registers, latches, electrically erasable programmable read only memory devices (EEPROM), not AND (NAND) flash memory devices, not OR (NOR) flash memory devices, non-volatile random access memory devices (NVRAM), synchronous dynamic random access memory (SDRAM devices, RAMBUS dynamic random access memory (RDRAM) devices, double data rate (DDR) memory devices, static random access memory (SRAM), universal serial bus (USB) removable memory, PCMCIA memory CANS, and the like; optical devices, such as compact disk read-write memory (CD ROM), and the like; and magnetic devices, such as a hard disk, a floppy disk, a magnetic tape, and the like.

A non-exhaustive list of data stored in memory areas 57 may include, for example, a sensing device identification code, device type or serial number, an illumination mode, analog gain, a transmission or sensory data gathering rate, or other device operation modes.

A non-exhaustive list of examples of power source 34 includes batteries, such as, for example, silver oxide batteries, lithium batteries, capacitors, or any other suitable power source. In another embodiment of the present invention, power source 34 may not be present and the device 4 may be powered by an external power source, for example, by a magnetic field or electric field that transmits to the device.

A non-exhaustive list of examples of imagers 40 includes a solid state imaging sensor, a complementary metal oxide semiconductor (CMOS) imaging sensor, a charge coupled device (CCD) imaging sensor, a linear imaging sensor, a line imaging sensor, a full frame imaging sensor, a "camera on chip" imaging sensor, or any other suitable imaging sensor. A 256×256, 256×262 or 320×320 pixel imager 40 may be used. In some embodiments, the dimensions of a frame produced by the imager may be different than the size of the data that the imager collects. For example, an imager that collects data corresponding to a 320×320 pixel grid may produce or transmit a 256×256 pixel frame. Pixel size may be, for example, between 5 and 6 micron. According to some embodiments each pixel may be fitted with a micro lens. Other numbers and dimensions may be used.

A non-exhaustive list of examples of workstations 8 includes an original equipment manufacturer (OEM) dedicated work station, a desktop personal computer, a server computer, a laptop computer, a notebook computer, a handheld computer, and the like.

Control block 26 may control, at least in part, the operation of sensing device 4. For example, control block 26 may synchronize time periods, in which illumination source 38 produces light rays or pulses, time periods, in which imager 40 captures images, and time periods, in which transmitter 28 transmits the images. In addition, control block 26 may produce timing signals and other signals necessary for the operation of transmitter 28, optional receiver 30 and imager 40. Moreover, control block 26 may perform operations that are complimentary to the operations performed by other components of sensing device 4, such as, for example, image-data buffering. Information in memory areas 57 may control the mode or settings for control block 26, processor 47 or imager 40.

Control block 26 may include any combination of logic components, such as, for example, combinatorial logic, state machines, controllers, processors, memory elements, and the like.

Control block 26, transmitter 28, optional receiver 30 and imager 40 may be implemented on any suitable combination of semiconductor dies or chips. For example, and although the invention is not limited in this respect, control block 26, transmitter 28 and optional receiver 30 may be parts of a first semiconductor die or chip, and imager 40 may be a part of a second semiconductor die. Such a semiconductor die may be an application-specific integrated circuit (ASIC) or may be part of an application-specific standard product (ASSP). According to some embodiments semiconductor dies may be stacked. According to some embodiments some or all of the components may be on the same semiconductor die.

Illumination source 38 may produce light pulses 44 that may penetrate through optical window 36 and may illuminate an inner portion 46 of a body lumen. A non-exhaustive list of examples of body lumens includes the gastrointestinal (GI) tract, a blood vessel, a reproductive tract, or any other suitable body lumen.

Reflections 50 of light pulses 44 from inner portion 46 of a body lumen may penetrate optical window 36 back into sensing device 4 and may be focused by optical system 42 onto imager 40. Imager 40 may receive the focused reflections 50, and in response to an image capturing command 52 from control block 26, imager 40 may capture an image of inner portion 46 of a body lumen. Control block 26 may receive the image of inner portion 46 from imager 40 over wires 54, and may control transmitter 28 to transmit the image of inner portion 46 through antenna 32 into wireless medium 11. Optional processor 47 may modify control block 26 operations. A component of system 2, external to sensing device 4, may modify control block 26 operations, for example, by setting memory areas 57. For example, workstation 8 or receiver/recorder 6 may transmit commands or mode information from transmitter. 62, via wireless or hard-wired medium 13 to receiver 30. The commands may cause control block 26 to modify operations, for example, to generate commands 52 that comply with the transmitted commands.

Sensing device 4 may passively or actively progress along a body lumen. Consequently, a stream of images of inner portions of a body lumen may be transmitted from sensing device 4 into wireless medium 11.

Sensing device 4 may transmit captured images embedded in, for example, "wireless communication frames". A payload portion of a wireless communication frame may include a captured image or other sensing data and may include additional data, such as, for example, data stored in memory areas 57, cyclic redundancy code and/or error correction code. In addition, a wireless communication frame may include an overhead portion that may contain, for example, framing bits, synchronization bits, preamble bits, and the like.

Figure 2:
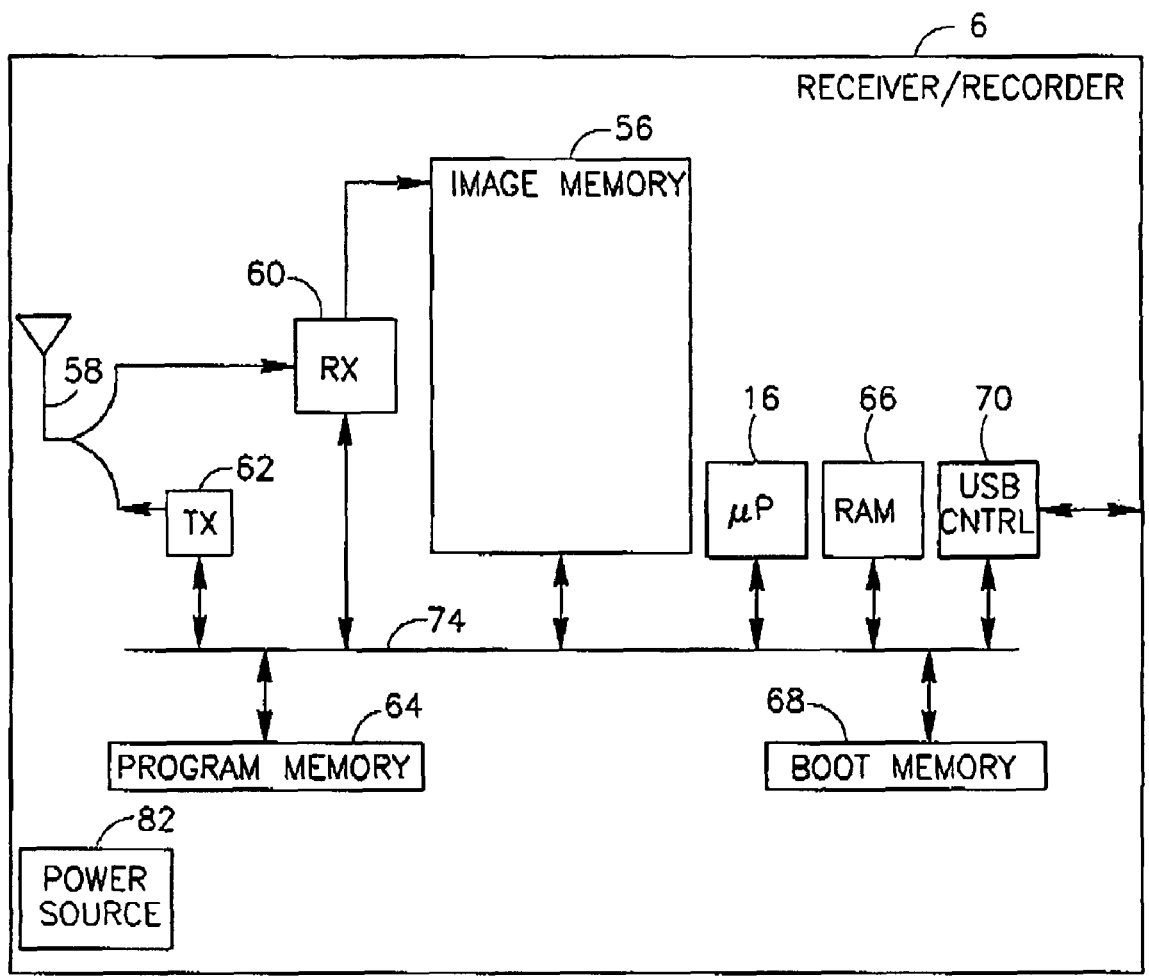
FIG. 2 is a simplified block-diagram illustration of a receiver/recorder of an in-vivo sensing system, in accordance with some embodiments of the invention.

Optional receiver 30 may receive wireless messages via wireless medium 11 through antenna 32, and control block 26 may capture these messages. A non-exhaustive list of examples of such messages includes modifying the states of sensing device 4, that may be stored in memory areas 57, for example, activating or de-activating image capturing by sensing device 4, controlling the time intervals for capturing images, activating or de-activating transmissions from sensing device 4, or any other suitable messages: Reference is made to FIG. 2, which is an exemplary simplified block-diagram illustration of receiver/recorder 6, in accordance with some embodiments of the invention.

Receiver/recorder 6 may include a memory 56, a processor 16, an antenna 58, a receiver (Rx) 60, an optional transmitter (TX) 62, a program memory 64, a random access memory (RAM) 66, boot memory 68, a power source 82, and a communication controller, such as, for example, a universal serial bus (USB) controller 70. According to other embodiments of the invention, transmitter 62 may be a unit separate from receiver/recorder 6.

Processor 16 may control the operation of receiver 60, optional transmitter 62, and USB controller 70 through, for example, a bus 74. In addition, receiver 60, optional transmitter 62, processor 16 and USB controller 70 may be able to exchange data, such as, for example, images received from sensing device 4, or portions thereof, over bus 74. It may be appreciated, that other methods for control and data exchange are possible, and are under the scope of the invention.

One or more antenna(s) 58 in sensing device 4 may be mounted inside or outside receiver/recorder 6 and both receiver 60 and optional transmitter 62 may be coupled to antenna 58. Optional transmitter 62 may be able to transmit wireless messages to sensing device 4 through antenna 58. Receiver 60 may be able to receive transmissions, such as, for example, a stream of wireless communication frames and support data, from sensing device 4 through antenna 58.

Selected bits of wireless communication data, for example, image data, memory data or corresponding image frames received by receiver 60 may be stored in memory 56.

Receiver/recorder 6 may communicate with workstation 8 via connection or medium 12. For example, receiver/recorder 6 may be able to transfer bits of wireless communication, for example, image data, memory data or corresponding image frames that are stored in memory 56 to workstation 8, and may receive controls, and other digital content, from workstation 8. Although the invention is not limited in this respect, medium 12 may be, for example, a USB cable and may be coupled to USB controller 70 of receiver/recorder 6. Alternatively, medium 12 may be wireless, and receiver/recorder 6 and workstation 8 may communicate wirelessly.

A non-exhaustive list of examples of image memory 56 and program memory 64 includes, for example, semiconductor devices such as registers or memory areas, latches, electrically erasable programmable read only memory devices (EE-PROM), not AND (NAND) flash memory devices, not OR (NOR) flash memory devices, non-volatile random access memory devices (NVRAM), synchronous dynamic random access memory (SDRAM) devices, RAMBUS dynamic random access memory (RDRAM) devices, double data rate (DDR) memory devices, static random access memory (SRAM), universal serial bus (USB) removable, memory, PCMCIA memory CANS, and the like; optical devices, such as compact disk read-write memory (CD ROM), and the like; and magnetic devices, such as a hard disk, a floppy disk, a magnetic tape, and the like.

A non-exhaustive list of examples of processor 16 includes a micro-controller, a micro, processor, a central processing unit (CPU), a digital signal processor (DSP), a reduced instruction set computer (RISC), a complex instruction set computer (CISC), and the like. Moreover, processor 16 may be part of an application specific integrated circuit (ASIC), may each be a part of an application specific standard product (ASSP), may be part of a field programmable gate array (FPGA), or may be a part of a complex programmable logic devices. (CPLD).

A non-exhaustive list of examples of antennae 32 and 58 includes dipole antennae, monopole antennae, multilayer ceramic antennae, planar inverted-F antennae, loop antennae, shot antennae, dual antennae, omni-directional antennae, coil antennae or any other suitable antennas. Moreover, antenna 32 and antenna 58 may be of different types.

Figure 3:
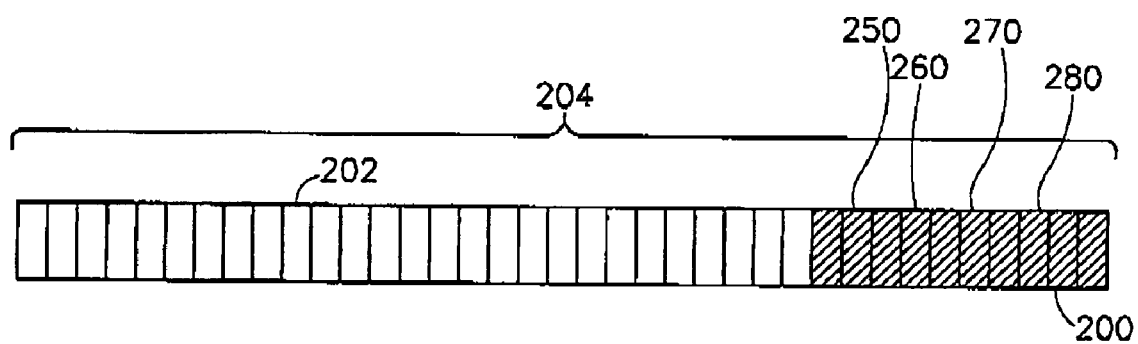
FIG. 3 is a schematic diagram of a block of data that may include memory data in accordance with an exemplary embodiment of the invention.

Reference is made to FIG. 3, which is a schematic diagram of a data block that may include memory data in accordance with an exemplary embodiment of the present invention. In some embodiments, data such as, for example, sensory data or image data that may have been collected by a sensing device 4 may be packaged or collected into blocks, for example, block 204. Data block 204 may be transmitted, for example, by transmitter 28 and received, for example, by receiver/recorder 6. Depending on communication protocols, data block 204 may be transmitted in one or more packages of suitable size. Data block 204 may include data stored in one or more memory areas 57 and/or image data generated by sensing device 4. Image data may be transmitted in sub-block 202 and memory data may be transmitted as added or attached data to a data block, for example, sub-block 200. For example, memory data, transmitted in sub-block 200 may relate to data stored in memory areas 57, substantially at the time sensing device 4 generated the image data in data block 204. In one embodiment, data from a specific memory area 57 may be transmitted at fixed time or location, for example, in sub-block 200, during each transmission of memory data.

In one embodiment, the transmitted memory data may be a fixed size data unit that may include the values or states of some or all memory areas 57 located in sensing device 4. Data block 204 may be any suitable length or size. While the length or size of data block 204 is typically fixed across imaging periods, it may vary in some embodiments and/or transmissions.

The location within sub-block 200 at which data from a specific memory area 57 is transmitted may depend on the use, type, mode or content of the specific memory area 57. For example, memory areas 57 that may be most frequently updated may be transmitted in contiguous times, addresses or positions in sub-block 200.

In one embodiment, memory data may be attached to and/ or transmitted with every or substantially every image data transmission from sensing device 4 to receiver/recorder 6. For example, substantially every transmitted data block 204 that includes image data, may also include a set of memory data. In some-embodiments, the same memory data is sent with each frame, and this may be a subset of the data stored in sensing device 4. For example, only static data such as serial number data may be sent with each data block 204. In other embodiments, memory data may be transmitted on its own and/or instead of transmission of an image frame, e.g. during a time window and/or period where an image frame may usually be transmitted.

Transmitting memory data with substantially every image data transmission may enable workstation 8 to use the memory data to efficiently monitor every image frame. In some embodiments of the present invention, relatively low data transmission rates may be used, for example, in accordance with regulations. In such embodiments, requests for data by a component of system 2 external to sensing device 4, from sensing device 4 may increase power consumption, may be temporally expensive, or may take time, where time constraints may be an issue. For example, if memory data is not transmitted automatically or substantially simultaneously to the transmission of corresponding image data, for example, if memory data is transmitted in response to a request from a component external to sensing device 4, the memory data may be transmitted with a delay. In some embodiments of the present invention, since the memory data is attached to the corresponding image data, the memory data is received by a program or viewer without delays associated with requests for data from sensing device 4. The memory data and the corresponding stream of images may be displayed substantially simultaneously, for example, in real time. The memory data may be displayed, for example, on a display unit 14 of a workstation 8. Memory data may be displayed, for example, substantially simultaneously and/or adjacently to image data to which it may correspond or to which it may be tagged.

In some embodiments, memory data may be transmitted separately from sensory data For example, if sensory data corresponding to an image frame is not transmitted (e.g. due to functional error) the memory data corresponding to the image frame may still be transmitted.

Memory data may be stored in a memory bank external to sensing device 4, for example, receiver/recorder 6, workstation 8 or another suitable storage unit of system 2. The memory data may be used at a time after the data block is transmitted, for example, during a stage of image data processing or viewing. The memory data may be marked or tagged to indicate to which data block 204 or stream of image data the memory data corresponds.

Typically, sensing device 4 transmits data in discrete portions. Each portion typically corresponds to an image or frame and may include memory data corresponding to the image or frame. For example, sensing device. 4 may capture an image once every half second, and, after capturing such an image, transmit the image to receiver/recorder 6 as an encoded image possibly over a series of imaging and transmission periods. Other constant and/or variable capture rates and/or transmission rates may be used. Typically, the image data recorded and transmitted is digital color image data, although in alternate embodiments other image formats (e.g., black and white image data) may be used. In one embodiment, each frame of image data includes 320 rows of 320 pixels each, each pixel including data for color and brightness, according to known methods. Other data formats may be used. For example, sensing device 4 may transmit sensory data captured, for example, by imager 40. Such data may include, for example, in-vivo physiological data, which may be transmitted as an electrical current, a voltage, etc. Other transmission methods may be used.

In some embodiments, sub-block 200 and sub-block 202 may have a fixed size or number of bytes corresponding to the, for example, 256×256 or 320×320 pixel image frame. In one embodiment, data corresponding to each pixel in the image frame may have a fixed size, for example, 8 bits or 12 bits. For example, data in sub-block 200 and sub-block 202 corresponding to the image frame may include 1×262 pixels and 256×262 pixels or 1×320 pixels and 320×320 pixels, respectively. Other block sizes or data formats may be used.

A processor such as, for example, processing unit 47 or another component that may be included in sensing device 4 may add an additional one or more bits or bytes (or other data units) to data block 204 that may include memory data and possibly additional data. The bytes (or other data units) including memory data may be included in sub-block 200. In FIG. 3 sub-block 200 is located at the end of data block 204 for illustrative purposes, however, bytes including memory data may be located in other locations within data block 204. For example, memory data may be prefix data, located at the beginning of data block 204.

If sub-block 200 is located at the end of data block 204, for example, memory data is attached or added to a stream of image data at the end of the set of data, it may be used, for example, by receiver/recorder 6, as a signal or indicator that the transmission of data corresponding to an image, a frame or stream of image data has ended.

Blocks of data 204 may be transmitted, for example, by transmitter 28 to a receiver/recorder 6. Receiver/recorder 6 may decode, reconstruct, display or otherwise process the data, or such operations (or a portion of such operations) may be performed by a unit to which receiver 6 writes the received data such as a processor in a workstation 8.

According to embodiments of the present invention, workstation 8 may display, store, process or use memory data in any suitable way. In one embodiment, memory data may be stored, for example, in workstations 8.

In one embodiment, the memory data may be used, for example, by a processor in workstation 8, to generate instructions or modify commands for sensing device 4, for example, as determined by the software or programs' codes. These commands may be sent to control receiver 30 of image device 4 via a transmitter, for example transmitter 62, where control block 26 may accept the commands and modify its operations accordingly to generate commands 52. In another embodiment, memory data may be used to alter or manipulate the processing of corresponding sensory data. For example, memory data may include instructions to a processor in workstation 8 that may indicate in what manner to display and/or process the corresponding sensory data.

In another embodiment, memory data or values or a derivation or representation thereof may be displayed on display 14, for example, in real time, so that a viewer may observe the state of the sensing device 4 in real time. The viewer may monitor or control sensing device 4 or alter sensing device commands 52, based on the memory data or image data displayed. For example, commands 52 may include settings for changing modes of operation, sending device identification, etc.

Certain portions of sub-block 200 may include for example scrambling data, which may protect data stored in memory areas 57.

The arrangement of data in a sub-block 200 may depend on the type of memory area 57 in which the data is stored. Similar types of data stored in memory areas 57 may be grouped in a specific portion of sub-block 200 that may, for example, have a fixed size and position in sub-block 200. For example, sum data, pixel sampling data, pixel difference data and error detection or correction data may be transmitted in portions 250, 260, 270 and 280 of sub-block 200, respectively. Portions 250, 260, 270 and 280 of sub-block 200 may be arranged in any order in sub-block 200. Other data that may or may not be stored in memory areas 57 may be transmitted adjacent to or in between portions 250, 260, 270 and 280 of sub-block 200.

Each memory area 57 or group of memory areas 57 may be associated with a specific segment, data group or portion of sub-block 200. Thus, system 2 components may automatically identify the locations of the memory areas 57 where data transmitted in sub-block 200 may be stored and may update, modify or correct the memory areas 57, by specifying only specific segment, data group or portion of sub-block 200. For example, different memory areas 57 of sensing device 4 may store different types of data, such as sum data, pixel sampling data, pixel difference data and/or other non-sensory data. Other types of memory areas 57, with other data content, may be used.

Sum data may be defined as and/or may include information regarding, for example, the total or sub-total number of pixels in an image frame that are a specified or predefined, one or more colors or color range. For example, the sum data may indicate the total number of pixels that may be predominantly red, green and/or blue in a set of image data (e.g., image data corresponding to a frame or transmitted in the same imaging period or data block as the sum data). Other colors may be represented in the sum data. The sum data may be defined over a specified area or portion of an image frame. In another embodiment, pixel difference data may be defined as and/or may include information regarding differences or changes in the sum data over one or more frames. For example, pixel difference data may indicate the difference in the number of pixels that are predominantly red, green and/or blue, between current and past image frames.

Pixel sampling data may relate to a sampled portion of an image frame, for example, a decimated image. For example, pixel sampling data may be a summary or sketch of an image frame. Pixel sampling data may be displayed as a thumbnail or may be used to construct a color bar. Pixel sampling data typically includes fewer data units than the corresponding image frames, allowing a user to access a sample of the corresponding images without processing and/or displaying the images in full. For example, pixel sampling data may indicate an average of data samplings (e.g., an average pixel value over one or more specified areas) of a pixel array or image frame. Pixel sampling data may include average measurements of intensities, color or other properties of pixels in sample areas of the pixel array. Pixel sampling data may be measured, recorded or calculated, for example, by imager 40, processor 47 or other components in sensing device 4.

Figure 4:
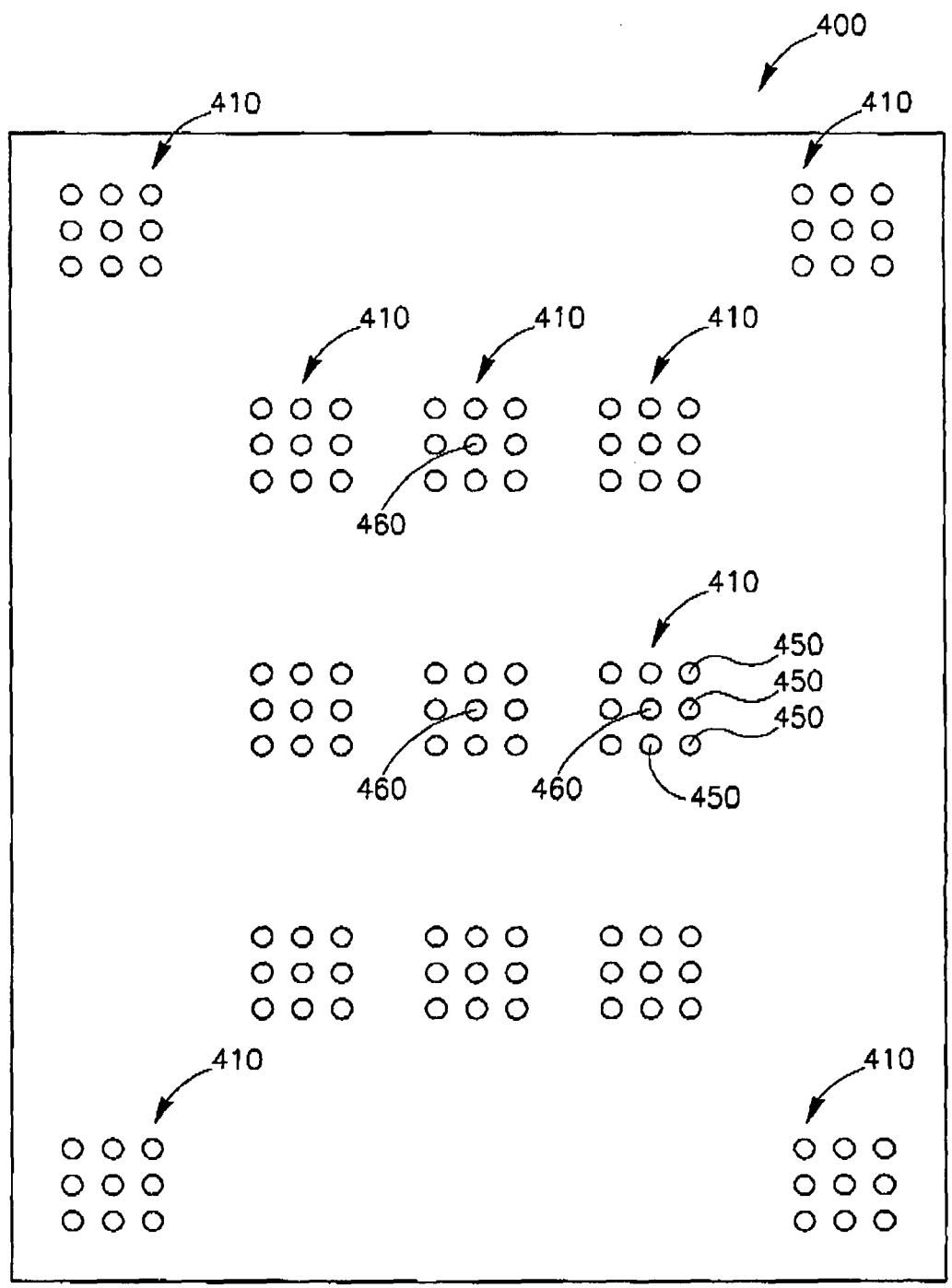
FIG. 4 is a schematic diagram of a sampling scheme in accordance with an exemplary embodiment of the invention.

FIG. 4 is a schematic diagram of a sampling scheme in accordance with an exemplary embodiment of the invention. In one embodiment, pixel sampling data corresponding to an image frame 400 may include a fixed number of sample areas 410 comprising one or more pixels 450 sampled from image frame 400. Sample areas 410 may have a fixed size (e.g., a 3 pixel by 3 pixel area) and location (e.g., centered at row 52, column 73 of a 256 pixel by 262 pixel frame). For example, the locations of center pixels 460 of sample areas 410 may be evenly distributed, for example, positioned along indices of image frame 400 in a grid or lattice configuration. Other sample areas 410 may be located at the corners of image frame 400. In one embodiment, there may be one pixel sampling data value associated with each sample area 410. Pixel sampling data may include the location of the sample areas 410 of image frame 400, for example, by indicating the coordinates of center pixels 460 and/or the dimensions of sample areas 410. In one embodiment, pixel sampling data may be stored or transmitted, for example, in the order that sample area 410 is positioned along the grid or lattice of image frame 400.

Figure 5:
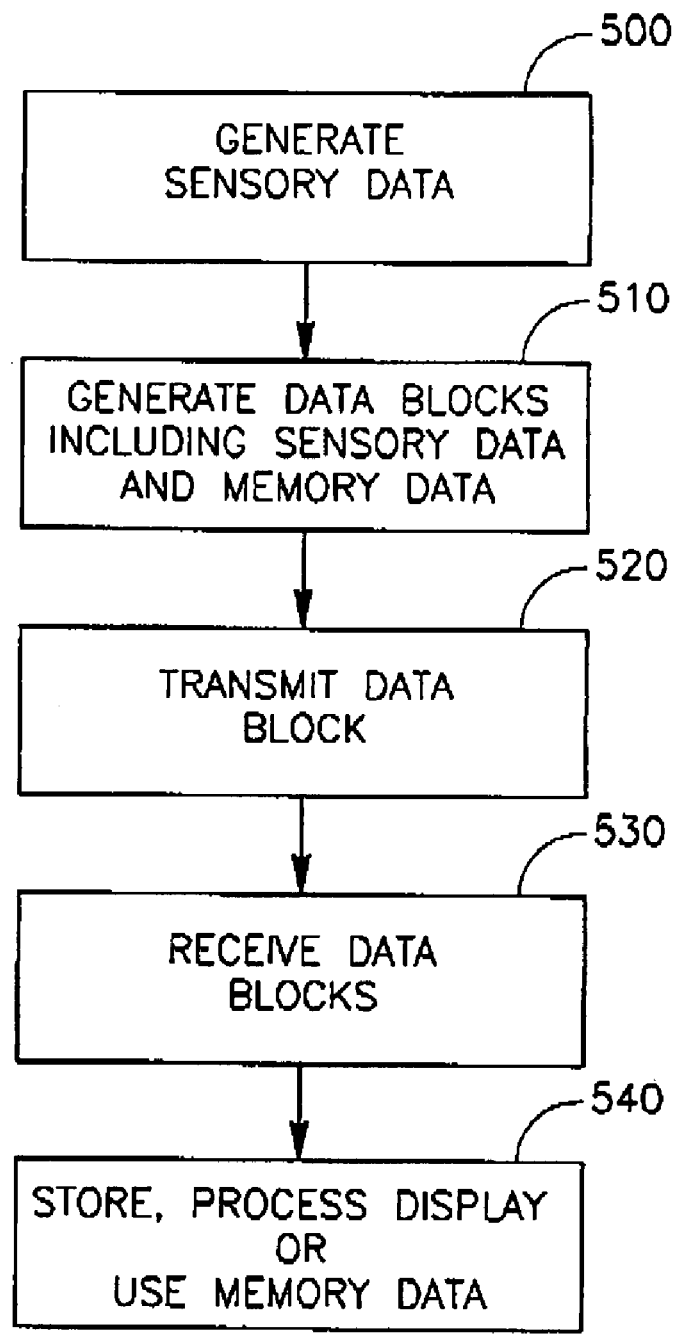
FIG. 5 is a flowchart of a method according to one embodiment of the present invention.

FIG. 5 is a flowchart of a method according to one embodiment of the present invention.

In operation 500, an in-vivo sensing device may generate sensory data. For example, a swallowable capsule may capture image data. Sensory data may include, for example, image data generated using an imaging system. In other embodiments, sensory data may include, for example, data relating to pH, temperature, pressure, electrical impedance, etc.

In operation 510, an in-vivo sensing device may generate data blocks that include sensory data and memory data. The sensory data may include data generated in operation 500. The memory data may be stored in memory areas in the sensing device, for example, in registers in an imager or transmitter in the sensing device.

In operation 520, a transmitter may transmit data blocks. Data block may include data blocks generated in operation 510. The transmitter may be located inside the in-vivo sensing device. The transmitter may transmit the data blocks via a wireless or hard-wired medium. In another embodiment, a transmitter, for example, in the sensing device, may transmit sensory data generated by the sensing device and non-sensory data stored in the sensing device, for example, in one or more memory areas. The transmitter may transmit sensory data and non-sensory data in the same imaging period, data blocks or image streams.

In operation 530, a receiver/recorder may receive data blocks. The receiver/recorder may receive data blocks transmitted in operation 520.

In operation 540, an in-vivo sensing system may store, process, display or use memory data. The memory data, for example, non-sensory data and the sensory data may be stored, processed, displayed or used separately or in combination.

Other operations or series of operations may be used.

It will be appreciated by persons skilled in the art that the present invention is not limited to what has been particularly shown and described hereinabove. Rather the scope of the present invention is defined only by the claims, which follow:

The invention claimed is:

1. A method for transmitting data from an in-vivo device, the in-vivo device operating across a series of imaging periods, the method comprising:
within an imaging period,
generating within the in-vivo device image data for an image captured by an array of image pixels in the in-vivo device;
sampling, from said captured image, decimated image data, said decimated image data comprising fewer data units than are in said captured image;
producing within the in-vivo device an image frame data block from the image data, wherein said image frame data block comprises both a first sub-block comprising image data and a second, separate sub-block comprising said decimated image data;
transmitting the image frame data block, wherein both said first sub-block comprising image data and said second sub-block comprising decimated image data are part of said image frame data block, from the in-vivo device;
receiving the transmitted image frame data block at a location remote from said in-vivo device;
processing data contained in the transmitted image frame data block;

generating a command based on said processed data; and transmitting the command to the imaging device.

2. The method of claim 1, wherein the imaging device is a swallowable imaging capsule.

3. The method of claim 1, wherein the decimated image data includes average pixel values of the one or more areas of the array of image pixels.

4. The method of claim 3, wherein the average pixel values include average measurements of intensities or color properties of the decimated image pixels.

5. The method of claim 1, wherein the decimated image data includes the total number of pixels in the array of image pixels that correspond to one or more predefined color ranges.

6. The method of claim 1, wherein the decimated image data includes information regarding differences in the total number of pixels that correspond to one or more predefined color ranges over one or more arrays of image pixels.

* * * * *